(12) United States Patent
Lewis et al.

(10) Patent No.: US 11,484,875 B2
(45) Date of Patent: Nov. 1, 2022

(54) PROCESS FOR REMOVING MERCURY IONS FROM BODILY FLUIDS USING TITANIUM METALLATE ION EXCHANGE COMPOSITIONS

(71) Applicant: UOP LLC, Des Plaines, IL (US)

(72) Inventors: Gregory John Lewis, Santa Cruz, CA (US); Paulina Jakubczak, Elk Grove Village, IL (US); Julio C. Marte, Carol Stream, IL (US); William Christopher Sheets, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 216 days.

(21) Appl. No.: 16/506,419

(22) Filed: Jul. 9, 2019

(65) Prior Publication Data

US 2021/0008537 A1 Jan. 14, 2021

(51) Int. Cl.
  B01J 20/00 (2006.01)
  B01J 39/02 (2006.01)
  A61M 1/28 (2006.01)
  A61K 45/06 (2006.01)

(52) U.S. Cl.
  CPC ........... B01J 39/02 (2013.01); A61M 1/28 (2013.01)

(58) Field of Classification Search
  CPC .... A61K 2300/00; A61K 33/24; A61K 33/00; A61K 45/06; A61K 9/143; A61K 9/14; A61K 9/2054; A61K 9/0095; A61K 9/10; A61K 9/16; A61K 9/20; B01J 39/14; B01J 39/02; B01J 19/0013; B01J 19/006; B01J 2219/00063; B01J 2219/00094; B01J 2219/00768; B01J 19/18; B01J 19/0066; B01J 39/10; B01J 41/10; B01J 20/10; B01J 20/02; B01J 20/186; B01J 2208/00017; B01J 41/02; B01J 8/1836; B01J 8/24; B01J 47/007; B01J 47/018; A61P 3/12; A61P 7/08; A61P 3/14; A61P 7/10; A61P 9/04; A61P 9/00; A61P 7/00; A61P 9/06; A61P 13/12; A61P 39/00; A61P 21/00; A61P 21/02; A61P 25/00; A61P 25/08; A61P 37/06; A61P 39/02; A61P 3/10
  USPC ......................................................... 210/638
  See application file for complete search history.

(56) References Cited

U.S. PATENT DOCUMENTS

| | | | |
|---|---|---|---|
| 4,261,828 A | 4/1981 | Brunner et al. | |
| 4,581,141 A | 4/1986 | Ash | |
| 5,536,412 A | 7/1996 | Ash | |
| 5,885,925 A * | 3/1999 | DeFilippi | G21F 9/125 502/427 |
| 5,888,472 A | 3/1999 | Bem et al. | |
| 5,891,417 A | 4/1999 | Bem et al. | |
| 6,099,737 A | 8/2000 | Sherman et al. | |
| 6,110,378 A * | 8/2000 | Anthony | C01B 39/085 210/682 |
| 6,332,985 B1 * | 12/2001 | Sherman | A61M 1/28 210/638 |
| 6,436,294 B2 | 8/2002 | Lundquist | |
| 6,579,460 B1 | 6/2003 | Willis et al. | |
| 6,616,860 B1 | 9/2003 | Onodera et al. | |
| 6,814,871 B1 | 11/2004 | Bem et al. | |
| 8,802,152 B2 | 8/2014 | Keyser et al. | |
| 8,808,750 B2 | 8/2014 | Keyser et al. | |
| 8,877,255 B2 | 11/2014 | Keyser et al. | |
| 9,150,436 B2 | 10/2015 | Lewis et al. | |
| 9,233,856 B2 | 1/2016 | Lewis et al. | |
| 9,457,050 B2 | 10/2016 | Keyser et al. | |
| 9,662,352 B2 | 5/2017 | Keyser et al. | |
| 9,707,255 B2 | 7/2017 | Keyser et al. | |
| 9,844,567 B2 | 12/2017 | Keyser et al. | |
| 9,861,658 B2 | 1/2018 | Keyser et al. | |
| 9,943,637 B2 | 4/2018 | Keyser et al. | |
| 2014/0311986 A1 | 10/2014 | Lewis et al. | |
| 2015/0225249 A1 | 8/2015 | Keyser et al. | |
| 2016/0038538 A1 | 2/2016 | Keyser et al. | |
| 2016/0000825 A1 | 7/2016 | Keyser et al. | |
| 2016/0271174 A1 | 9/2016 | Keyser et al. | |
| 2018/0214479 A1 | 8/2018 | Keyser et al. | |

FOREIGN PATENT DOCUMENTS

| | | |
|---|---|---|
| CA | 1328099 C | 3/1994 |
| EP | 0046971 A1 | 3/1982 |

OTHER PUBLICATIONS

PCT International Search Report and Written Opinion for PCT/US2020/040238 dated Jan. 20, 2022.
Medvedev Dmitri G. et al., Crystallization of Sodium Titanium Silicate with Sitinakite Topology: Evolution from the Sodium Nonatitanate Phase. Chem. Mater., 2004, vol. 16, No. 19, p. 3659-3666.
Ash et al., "A phase 2 study on the treatment of hyperkalemia in patients with chronic kidney disease suggests that the selective potassium trap, ZS-9, is safe and efficient", Clinical Trial, Kidney International, International Society of Nephrology, 2015.
Baxter et al., Pediatric fatality secondary to EDTA chelation, Clinical Toxicology, 46:10, 1083-1084, 2008.

(Continued)

*Primary Examiner* — Allison G Fitzsimmons
(74) *Attorney, Agent, or Firm* — Paschall & Associates, LLC; Mark Goldberg

(57) ABSTRACT

A process for removing $Hg^{2+}$ toxins from bodily fluids is disclosed. The process involves contacting the bodily fluid with a titanium metallate ion exchanger to remove the metal toxins in the bodily fluid, including blood and gastrointestinal fluid. Alternatively, blood can be contacted with a dialysis solution which is then contacted with the ion exchanger. The titanium metallate ion exchangers are represented by the following empirical formula:

$A_m TiNb_a Si_x O_y$.

A composition is provided with the combination of the titanium metallate ion exchanger and bodily fluids or dialysis solutions. Also, provided is an apparatus comprising a matrix and the titanium metallate ion exchanger.

20 Claims, No Drawings

(56) References Cited

OTHER PUBLICATIONS

Brown et al., Deaths Resulting From Hypocalcemia After Administration of Edetate Disodium: 2003-2005; Pediatrics, e534-e536, 2006.

Markowitz, Deaths Associated with Hypocalcemia from Chelation Therapy—Texas, Pennsylvania, and Oregon, 2003-2005, MMWR, pp. 204-206, 2006.

Atwood et al., In pediatric fatality, edetate disodium was no accident, Clinical Toxicology, 2009.

* cited by examiner

PROCESS FOR REMOVING MERCURY IONS FROM BODILY FLUIDS USING TITANIUM METALLATE ION EXCHANGE COMPOSITIONS

FIELD OF THE INVENTION

This invention relates to an extracorporeal or intracorporeal processes for removing $Hg^{2+}$ ions from bodily fluids. Blood or other bodily fluid is either contacted directly with a titanium metallate ion exchange composition which is capable of selectively removing the toxins from the blood or the blood or other bodily fluid is first contacted with a dialysis solution which is then contacted with the metallate ion exchange composition.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatine, ammonia, phenols, mercaptans, short chain fatty acids, aromatic amino acids, false neural transmitters (octopamine), neural inhibitors (glutamate) and bile salts. Among these, phenols and mercaptans, along with bilirubin and bacterial endotoxins, also occur as strong protein-bound toxins and are thus more difficult to effectively remove from the blood. Middle molecular weight toxins having a molecular weight of about 300 to about 10,000 can also be present and are difficult to effectively remove. The art shows a number of ways to treat blood containing such toxins. The classic method is of course dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today is similar to that developed by Kolff in the early 1940s. Since the 1940s there have been a number of disclosures which deal with improvements on artificial kidneys or artificial livers. Thus, U.S. Pat. No. 4,261,828 discloses an apparatus for the detoxification of blood. The apparatus comprises a housing filled with an adsorbent such as charcoal or a resin and optionally an enzyme carrier. To prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium-exchanged zeolite. EP 0046971 A1 discloses that zeolite W can be used in hemodialysis to remove ammonia. Finally, U.S. Pat. No. 5,536,412 discloses hemofiltration and plasma filtration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

These strategies can also be applied to removing $Hg^{2+}$ from the blood. Recently, several families of materials were shown to be effective in the remediation of $Hg^{2+}$ from aqueous solutions. U.S. Pat. No. 9,233,856 discloses medium charge density zeolites with Si/Al ratios preferably ranging from 3-10 that removed $Hg^{2+}$ selectively from aqueous solutions, even in the presence of $Mg^{2+}$ and $Ca^{2+}$. Similarly, U.S. Pat. No. 9,150,436 discloses a family of metallomanganese-based oxide ion exchangers that can remove $Hg^{2+}$ from aqueous solutions. Both crystalline and amorphous materials were effective, provided the theoretical ion exchange capacity per framework metal was between 0.08 and 0.25 negative charges per framework atom, corresponding to an intermediate range of framework charge density.

There are problems associated with the adsorbents disclosed in the above patents when it comes to treating blood and gastrointestinal fluids. For example, charcoal does not remove any water, phosphate, sodium or other ions. Zeolites have the disadvantage that they can partially dissolve in the dialysis solution, allowing aluminum and/or silicon to enter the blood. Additionally, zeolites can adsorb sodium, calcium and potassium ions from the blood thereby requiring that these ions be added back into the blood. On the other hand, the manganese oxides are oxidants that can be reduced by hydrochloric acid in gastrointestinal fluids and various components of the blood, releasing $Mn^{2+}$ ions. Gastrointestinal fluids may also attack Al in zeolites, releasing Al and some Si into the digestive tract.

More recently, examples of microporous ion exchangers that are essentially insoluble in fluids, such as bodily fluids (especially blood), have been developed, namely the zirconium-based silicates and titanium-based silicates of U.S. Pat. Nos. 5,888,472, 5,891,417 and 6,579,460. The use of these zirconium-based silicate or titanium-based silicate microporous ion exchangers to remove toxic ammonium cations from blood or dialysate is described in U.S. Pat. Nos. 6,814,871, 6,099,737, and 6,332,985. Additionally, it was found that some of these compositions were also selective in potassium ion exchange and could remove potassium ions from bodily fluids to treat the disease hyperkalemia, which is discussed in patents U.S. Pat. Nos. 8,802,152, 8,808,750, 8,877,255, 9,457,050, 9,662,352, 9,707,255, 9,844,567, 9,861,658, US 2015/0225249, US 20016/0000825, US 2016/0038538, US 2016/0271174 and US 2018/0214479. Ex-vivo applications of these materials, for instance in dialysis, are described in U.S. Pat. No. 9,943,637, which is incorporated in its entirety.

Mercury is known to adversely affect the nervous system and kidneys in humans. Mercury poisoning in humans occurs by exposure to one of three different forms of mercury, organomercury, inorganic mercury and elemental mercury. The most common exposure to organomercury comes from consumption of mercury tainted seafood. Inorganic mercury exposure includes ingestion of salts of mercury. A once very common route of mercury exposure was the inhalation of mercury vapor. The elemental mercury is efficiently adsorbed by the lungs and its high solubility in lipids enables diffusion across membranes to the blood. On entering cells, elemental mercury is oxidized to inorganic cationic mercury, $Hg^{2+}$ (See Autoimmunity Reviews, 2017, 16, 72-80).

Currently, chelating agents are used to treat mercury poisoning. DMSA, dimercaptosuccinic acid, and DMPS, 2,3-dimercaptopropanesulfonic acid, are dithiol-containing chelating agents that are water soluble that can be taken orally or intravenously (See Journal of Medical Toxicology, 2013, 9, 347-354). This was a great advantage over an earlier chelation treatment employing BAL, 2,3-dimercaptopropanol, which was not water soluble and administered by painful intramuscular injections. However, in the case of acute mercury intoxication, the chelators must be administered quickly after exposure or their effectiveness quickly diminishes. The benefit of these chelators in reducing mercury tissue content in chronic mercury intoxication is largely unestablished. Mobilization of mercury by chelation may also lead to redistribution of the mercury to other tissues.

Many ion-exchangers have been developed for removal of "heavy metals" from various streams, often waste streams. The heavy metals often include lead, mercury, cadmium, zinc, chromium, copper, cobalt, nickel and even arsenic. In many applications, these metals are lumped together as if they have the same ion-exchange properties, but in fact there is great variation. Zeolites are well known ion-exchangers and the ability of a particular zeolite to remove $Pb^{2+}$ from solution does not mean that it will remove $Hg^{2+}$ from solution. In U.S. Pat. No. 9,233,856 it is shown that the uptake of $Hg^{2+}$ by zeolites is highly dependent on the framework charge density or equivalently, the Si/Al ratio. High charge density Si/Al=1 zeolites like X (FAU topology) and 4A (LTA topology) are shown to have almost no affinity for $Hg^{2+}$ under the test conditions while they easily remove $Ca^{2+}$ and $Mg^{2+}$. In the same test using UZM-9, a zeolite with Si/Al=5.50 that has the same LTA zeolite topology as zeolite 4A, the situation is reversed and there is high selectivity for $Hg^{2+}$, while the selectivity to $Ca^{2+}$ and $Mg^{2+}$ is highly diminished. In the case of zeolite 4A and UZM-9, this result decouples structure from the framework charge density and shows the importance of the latter in ion-exchange selectivity. Meanwhile, our investigations show that zeolite X is excellent at removing $Pb^{2+}$ from aqueous solution, see comparative example 13 below, while it performs poorly at removing $Hg^{2+}$.

To remove $Hg^{2+}$ directly from blood, the ion-exchange material must be stable and insoluble in blood. Materials that fall into this category include titanium, zirconium and tin oxides and silicates, see U.S. Pat. No. 5,888,472. A sodium titanate ion-exchanger is disclosed in U.S. Pat. No. 5,885,925 that enumerates the metals and the applications where the ion-exchanger may be useful. There is no anticipation of utility in the healthcare, medical or pharmaceutical field. In fact, the conditions under which the ion-exchange testing were conducted included basic conditions, pH=9.95 to 11.4, and acidic conditions, pH=2.3. These conditions are very different than the pH of blood, which is about 7.4. Amorphous titanium and tin silicate ion-exchangers for removal of heavy metals from aqueous solutions are disclosed in U.S. Pat. No. 5,053,139, which focus on $Pb^{2+}$ removal from drinking water. Removal of $Pb^{2+}$, $Hg^{2+}$, $Cr^{3+}$ and $Cd^{2+}$ is demonstrated, but there is no anticipation of utility in the healthcare, medical or pharmaceutical field. A small pore titanium silicate with the same topology as the mineral zorite, ETS-4, is disclosed in CA 1,328,099 that claims to be proficient in removing $Hg^{2+}$ from aqueous solutions, however, the test conditions are ambiguous since the amount of ion-exchanger used in the test are not disclosed. A titanogermanosilicate ion exchanger that is an intergrowth of the pharmacosiderite and sitinakite structures disclosed in U.S. Pat. No. 5,935,552 is tested for $Cs^+$ uptake in concentrated hydroxide solution and does not anticipate application in the healthcare, medical or pharmaceutical field. A titanosilicate disclosed in U.S. Pat. No. 6,482,380B1 claims to be selective for remediation divalent ions from aqueous and hydrocarbon streams, but a data point for only $Sr^{2+}$ is disclosed without the test conditions. A list of possible applications is given, but healthcare, pharmaceutical and medical applications are not anticipated.

Applicants have developed a process which uses titanium metallate ion exchangers which are essentially insoluble in fluids, such as bodily fluids (especially blood) or dialysis solutions. These ion exchangers have an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" is the mole ratio of the framework oxide to Ti has a value from 2.05 to 11 and the titanium metallate ion exchangers consist of one of three topologies, sodium nonatitanate, sitinakite, acid treated zorite and mixtures thereof. Since these compositions are essentially insoluble in bodily fluids (at neutral and mildly acidic or basic pH), they can be orally ingested to remove toxins in the gastrointestinal system as well as used to remove toxins from blood, specifically, $Hg^{2+}$.

SUMMARY OF THE INVENTION

As stated, this invention relates to a process for removing toxins, specifically $Hg^{2+}$, from fluids selected from the group consisting of a bodily fluid, a dialysate solution and mixtures thereof, the process comprising contacting the fluid containing the toxins with an ion exchanger at ion exchange conditions thereby removing the toxins from the fluid, the titanium metallate ion exchanger selected from the group consisting of the sodium nonatitanate, sitinakite, acid-treated zorite topologies and mixtures thereof, the composite metallate having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11.

Another embodiment of the invention is a combination of a bodily fluid or dialysate solution and a titanium metallate ion exchanger selected from sodium nonatitanate, sitinakite and acid-treated zorite topologies, the composite metallate having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11.

Another embodiment of the invention is an apparatus incorporating a titanium metallate ion exchanger selected from sodium nonatitanate, sitinakite and acid-treated zorite topologies, the composite metallate having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11. The apparatus is configured to contact a bodily fluid or a dialysate solution to remove ions selected from $Co^{2+}$, $Pb^{2+}$, $Cd^{2+}$ and $Cr^{3+}$. The apparatus of the present invention that contains the above described metallate ion exchanger may be a sorption filter on a wearable device or a device that is remote to the individual. The metallate ion exchanger may be supported or embedded in a porous biocompatible matrix, including polymers and porous and mesoporous metal oxides and silicates. Natural or biopolymers such as cross-linked carbohydrates or proteins are in particular contemplated as the useful polymers for the present invention.

These and other objects and embodiments will become more clear after a detailed description of the invention.

DETAILED DESCRIPTION OF THE INVENTION

As stated, applicants have developed a new process for removing $Hg^{2+}$ from fluids selected from bodily fluids and dialysate solution. One essential element of the instant process is an ion exchanger which has a large capacity and strong affinity, i.e., selectivity for $Hg^{2+}$. These compositions are identified as having the sodium nonatitanate topology, sitinakite topology or an acid treated zorite topology or mixtures thereof. They are further identified by their composite empirical formula (on an anhydrous basis) which is:

$$A_m TiNb_a Si_x O_y$$

The composition has a framework structure(s) composed of at least $TiO_{6/n}$ octahedral units where n=2 or 3 or both, optionally $NbO_{6/n}$ octahedral units where n=2 or 3 or both, and optionally $SiO_2$ tetrahedral units. A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11.

The titanium metallates, optionally containing one or more of niobium and silicon and mixtures thereof are prepared by a hydrothermal crystallization of a reaction mixture prepared by combining a reactive source of titanium, optionally a source of Nb, optionally a Si source and at least one alkali metal and water. The alkali metal acts as a templating agent. Any titanium compound, which can be hydrolyzed to titanium oxide can be used. Specific examples of titanium metal sources include, but are not limited to titanium alkoxides, titanium tetrachloride, titanium trichloride and titanium dioxide. The sources of silica include colloidal silica, fumed silica, tetraethylorthosilicate and sodium silicate. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, and cesium halide. Specific examples of the Nb metal sources include niobium isopropoxide, niobium oxalate and hydrous niobium oxide. Generally, the hydrothermal process used to prepare the titanium metallate ion exchange compositions of this invention involves forming a reaction mixture which in terms of molar ratios of the oxides is expressed by the formula:

$$pA_2O:TiO_2:bNb_2O_5:cSiO_2:dH_2O$$

where "p" has a value from 0.25 to 10, "b" has a value from 0 to 0.3, "c" has a value from 0 to 6, and "d" has a value of 10 to 1000. The reaction mixture is prepared by mixing the desired sources of titanium, optionally silicon and optionally Nb metal, and alkali metal in any order to give the desired mixture. It is also necessary that the mixture have a basic pH and preferably a pH of at least 8. The basicity of the mixture is controlled by adding excess alkali hydroxide and/or basic compounds of the other constituents of the mixture, such as sodium silicate. Having formed the reaction mixture, it is next reacted at a temperature of about 50° C. to about 200° C. for a period of about 1 to about 30 days in a sealed reaction vessel under autogenous pressure. After the allotted time, the mixture is filtered to isolate the solid product which is washed with deionized water and dried in air. As stated, the compositions of this invention have a framework structure of octahedral $TiO_{6/n}$ units and optionally octahedral $NbO_{6/n}$ units, n=2 or 3, and optionally tetrahedral $SiO_2$ units. This framework often results in a microporous structure having an intracrystalline pore system with uniform pore diameters, i.e., the pore sizes are crystallographically regular. The microporous frameworks of this invention include the sitinakite and zorite topologies, with compositions of the zorite treatment requiring treatment with acid to be utilized. Compositions with the sitinakite topology may be employed as-synthesized or after treatment with acid. On the other hand, the framework of this composition may be layered as in the case of sodium nonatitanate. The titanium metallates of this invention must have one of these three topologies or consist of a mixture of these topologies.

As synthesized, the compositions of this invention will contain some of the alkali metal templating agent in the pores, between layers or in other charge balancing positions. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$), hydronium ion or mixtures thereof. It is understood that the A' cation is different from the A cation. The methods used to exchange one cation for another are well known in the art and involve contacting the ion exchange compositions with a solution containing the desired cation (at molar excess) at exchange conditions. Exchange conditions include a temperature of about 25° C. to about 100° C. and a time of about 20 minutes to about 2 hours. The particular cation (or mixture thereof), which is present in the final product will depend on the particular use of the composition and the specific composition being used. One specific composition is an ion exchanger where the A' cation is a mixture of $Na^+$, $Ca^{2+}$ and $H^+$ ions.

It is also within the scope of the invention that these ion exchange compositions can be used in powder form or can be formed into various shapes by means well known in the art. Examples of these various shapes include pills, extrudates, spheres, pellets and irregularly shaped particles. This has previously been demonstrated in U.S. Pat. Nos. 6,579,460 and 6,814,871.

As stated, these compositions have utility in adsorbing various metal toxins, specifically $Hg^{2+}$, from fluids selected from bodily fluids, dialysate solutions, and mixtures thereof. As used herein and in the claims, bodily fluids will include but not be limited to blood and gastrointestinal fluids. The treating of blood includes treating whole blood, blood plasma or other components of blood. Also by treating bodily fluids, it is meant to be in connection with any mammalian body including but not limited to humans, cows, pigs, sheep, monkeys, gorillas, horses, dogs, etc. The instant process is particularly suited for removing toxins from a human body. There are a number of means for directly or indirectly contacting the fluids with the desired ion exchanger and thus, remove the toxins. One technique is hemoperfusion, which involves packing the above described ion exchange composition into a column through which blood is flowed. One such system is described in U.S. Pat. No. 4,261,828. As stated in the '828 patent, the ion exchange composition is preferably formed into desired shapes such as spheres. Additionally, the ion exchange composition particles can be coated with compounds, such as cellulose derivatives, which are compatible with the blood but non-permeable for corpuscular blood components. In one specific case, spheres of the desired ion exchange compositions described above can be packed into hollow fibers thereby providing a semipermeable membrane. It should also be pointed out that more than one type of ion-exchange composition can be mixed and used in the process in order to enhance the efficiency of the process.

Another way of carrying out the process is to prepare a suspension or slurry of the molecular sieve adsorbent by means known in the art such as described is U.S. Pat. No. 5,536,412. The apparatus described in the '412 patent can also be used to carry out the process. The process basically involves passing a fluid, e.g. blood, containing the metal toxins through the interior of a hollow fiber and during said passing, circulating a sorbent suspension against the exterior surfaces of the hollow fiber membrane. At the same time, intermittent pulses of positive pressure are applied to the sorbent solution so that the fluid alternately exits and reenters the interior of the hollow fiber membrane thereby removing toxins from the fluid.

Another type of dialysis is peritoneal dialysis. In peritoneal dialysis, the peritoneal cavity or the abdominal cavity (abdomen) is filled via a catheter inserted into the peritoneal cavity with a dialysate fluid or solution which contacts the peritoneum. Toxins and excess water flow from the blood through the peritoneum, which is a membrane that surrounds the outside of the organs in the abdomen, into the dialysate fluid. The dialysate remains in the body for a time (dwell time) sufficient to remove the toxins. After the required dwell time, the dialysate is removed from the peritoneal cavity through the catheter. There are two types of peritoneal dialysis. In continuous ambulatory peritoneal dialysis (CAPD), dialysis is carried out throughout the day. The process involves maintaining the dialysate solution in the peritoneal cavity and periodically removing the spent dialysate (containing toxins) and refilling the cavity with a fresh dialysate solution that must be used for each exchange. This is carried out several times during the day. The second type is automated peritoneal dialysis or APD. In APD, a dialysate solution is exchanged by a device at night while the patient sleeps. In both types of dialyses, a fresh dialysate solution must be used for each exchange.

The titanium metallates of the present invention can be used to regenerate the dialysate solutions used in peritoneal dialysis, thereby further decreasing the amount of dialysate that is needed to cleanse the blood and/or the amount of time needed to carry out the exchange. This regeneration is carried out by any of the means described above for conventional dialysis. For example, in an indirect contacting process, the dialysate from the peritoneal cavity, i.e. first dialysate which has taken up metal toxins transferred across the peritoneum is now contacted with a membrane and a second dialysate solution and metal toxins are transferred across a membrane, thereby purifying the first dialysate solution, i.e. a purified dialysate solution. The second dialysate solution containing the metal toxins is flowed through at least one adsorption bed containing at least one of the ion exchangers described above, thereby removing the metal toxins and yielding a purified second dialysate solution. It is usually preferred to continuously circulate the second dialysate solution through the adsorbent bed until the toxic metal ions have been removed, i.e., $Hg^{2+}$. It is also preferred that the first dialysate solution be circulated through the peritoneal cavity, thereby increasing the toxic metal removal efficiency and decreasing the total dwell time.

A direct contacting process can also be carried out in which the first dialysate solution is introduced into the peritoneal cavity and then flowed through at least one bed containing at least one ion exchanger. As described above, this can be carried out as CAPD or APD. The composition of the dialysate solution can be varied in order to ensure a proper electrolyte balance in the body. This is well known in the art along with various apparatus for carrying out the dialysis.

The titanium metallates can also be formed into pills or other shapes which can be ingested orally and pick up toxins in the gastrointestinal fluid as the ion exchanger passes through the intestines and is finally excreted. To protect the ion exchangers from the high acid content in the stomach, the shaped articles may be coated with various coatings which will not dissolve in the stomach, but dissolve in the intestines. The ion exchange compositions of this invention may also be supported, ideally in a porous network including insertion into or binding to a blood compatible porous network such as in a sorption filter as disclosed in U.S. Pat. No. 9,033,908B2. The porous network may consist of natural or synthetic polymers and biopolymers and mesoporous metal oxides and silicates. Natural polymers (biopolymers) that are suitable may comprise a cross-linked carbohydrate or protein, made of oligomeric and polymeric carbohydrates or proteins. The biopolymer is preferably a polysaccharide. Examples of polysaccharides include α-glucans having 1, 3-, 1, 4- and/or 1, 6-linkages. Among these, the "starch family", including amylose, amylopectin and dextrins, is especially preferred, but pullulan, elsinan, reuteran and other uα-glucans, are also suitable, although the proportion of 1, 6-linkages is preferably below 70%, more preferably below 60%. Other suitable polysaccharides include β-1, 4-glucans (cellulose), β-1, 3-glucans, xyloglucans, glucomannans, galactans and galactomannans (guar and locust bean gum), other gums including heterogeneous gums like xanthan, ghatti, carrageenans, alginates, pectin, β-2, 1- and β-2, 6-fructans (inulin and levan), etc. A preferred cellulose is carboxymethylcellulose (CMC, e.g. AKUCELL from AKZO Nobel). Carbohydrates which can thus be used are carbohydrates consisting only of C, H and O atoms such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e.g., guar. Preferably, oligomeric carbohydrates with a degree of polymerization (DP) from DP2 on or polymeric carbohydrates from DP50 on are used. These can be naturally occurring polymers such as starch (amylose, amylopectin), cellulose and gums or derivates hereof which can be formed by phosphorylation or oxidation. The starch may be a cationic or anionic modified starches. Examples of suitable (modified) starches that can be modified are corn starch, potato starch, rice starch, tapioca starch, banana starch, and manioc starch. Other polymers can also be used (e.g. caprolactone). In certain embodiments, the biopolymer is preferably a cationic starch, most preferably an oxidized starch (for instance C6 oxidized with hypochlorite). The oxidation level may be freely chosen to suit the application of the sorbent material. Very suitably, the oxidation level is between 5 and 55%, most preferably between 25 and 35%, still more preferably between 28% and 32%. Most preferably the oxidized starch is crosslinked. A preferred crosslinking agent is di-epoxide. The crosslinking level may be freely chosen to suit the application of the sorbent material. Very suitably, the crosslinking level is between 0.1 and 25%, more preferably between 1 and 5%, and most preferably between 2.5 and 3.5%. Proteins which can be used include albumin, ovalbumin, casein, myosin, actin, globulin, hemoglobin, myoglobin, gelatin and small peptides. In the case of proteins, proteins obtained from hydrolysates of vegetable or animal material can also be used. Particularly preferred protein polymers are gelatin or a derivative of gelatin.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium or sodium, calcium and hydronium ions. The relative amount of sodium and calcium can vary considerably and depends on the ion exchange composition and the concentration of these ions in the blood.

The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer-based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks. As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In the x-ray patterns reported, the relative intensities of the d-spacings are indicated by the notations vs, s, m, and w which represent very strong, strong, medium, and weak, respectively. In terms of $100 \times I/I_o$, the above designations are defined as:

$w => 0\text{-}15; m > 15\text{-}60: s > 60\text{-}80$ and $vs > 80\text{-}100$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the instant invention, the following examples are set forth. It is to be understood that the examples are only by way of illustration and are not intended as an undue limitation on the broad scope of the invention as set forth in the appended claims.

EXAMPLES

Acid Treatment Procedure

Several of the test candidates were selected to undergo an acid wash. A 5 wt. % nitric acid solution was used targeting 2-3 g test material in 100 g exchange solution. Acid wash was performed in a three-stage exchange procedure at 75° C. for 1.5 hours each stage. Exchanged materials were isolated via filtration, washed thoroughly with deionized water and dried at 80° C.

Na Ion-Exchange Procedure

Materials not synthesized in the $Na^+$ form were sodium ion-exchanged prior to testing. Typically, a three-stage ion-exchange with NaCl was employed. The ion-exchange procedure consisted of exposing 5-10 g of product to be tested to 500 mL of 1-2 M NaCl exchange solution. Three ion-exchanges were performed at 75° C., stirring for 1.5 hours for each exchange step. Exchanged solids were isolated via filtration or centrifugation.

Example 1

A sodium nonatitanate, $Na_4Ti_9O_{20}$, was supplied by Honeywell and used as received. Characterization of the sample by powder x-ray diffraction was consistent with sodium nonatitanate. Representative x-ray diffraction lines for the sample are given in Table 1 below.

TABLE 1

| 2-Θ | d(Å) | I/I$_o$ % |
|---|---|---|
| 9.00 | 9.81 | vs |
| 18.08 | 4.90 | w |
| 24.38 | 3.65 | w |
| 24.40 | 3.65 | w |
| 28.12 | 3.17 | w |
| 29.01 | 3.08 | w |
| 33.83 | 2.65 | w |
| 34.70 | 2.58 | w |
| 39.94 | 2.26 | w |
| 44.33 | 2.04 | w |
| 44.63 | 2.03 | w |
| 47.70 | 1.91 | w-m |
| 48.34 | 1.88 | w-m |

Example 2

A solution was prepared by dissolving 29.07 g NaOH pellets (Fisher) in 815.27 g deionized water. With vigorous overhead stirring using a high-speed mechanical stirrer, 49.13 g colloidal silica (Ludox™ AS-40, 40% $SiO_2$) was added slowly but with a single pour. After about an hour of mixing, 106.53 g of $Ti(OiPr)_4$ (97%) was added quickly via a single pour to the colloidal translucent suspension immediately forming a precipitate. The reaction mixture was homogenized for an additional 5 minutes and loaded into a 2 L autoclave. The material was digested for 24 hours at 200° C. under static conditions. The product was isolated by centrifugation, washed 3 times with deionized water and dried in a 100° C. oven overnight. The product was characterized by X-ray diffraction, which identified the product as titanium silicate sitinakite. Representative x-ray diffraction lines for the product are shown in Table 2.

TABLE 2

| 2-Θ | d(Å) | $I/I_0$ % |
|---|---|---|
| 11.30 | 7.82 | vs |
| 17.85 | 4.97 | w |
| 26.68 | 3.34 | w |
| 27.25 | 3.27 | m |
| 27.68 | 3.22 | m-s |
| 32.30 | 2.77 | w |
| 34.50 | 2.60 | m |

Example 3

This UOP commercial sample, designated IE-910, has the sitinakite structure with anhydrous composition $Na_{3.24}Ti_{2.67}Nb_{1.18}Si_2O_{13.9}$. Representative diffraction lines for the material are shown in Table 11 below.

TABLE 11

| 2-Θ | d(Å) | $I/I_0$ % |
|---|---|---|
| 8.76 | 10.08 | w* |
| 10.00 | 8.84 | w* |
| 11.28 | 7.84 | vs |
| 14.71 | 6.02 | m |
| 15.90 | 5.55 | w |
| 17.60 | 5.03 | m |
| 18.00 | 4.92 | w* |
| 18.58 | 4.77 | w |
| 22.67 | 3.92 | w |
| 23.64 | 3.76 | w* |
| 25.26 | 3.52 | w |
| 26.46 | 3.37 | m |
| 27.42 | 3.25 | m |
| 29.63 | 3.01 | w |
| 30.25 | 2.95 | w* |
| 31.80 | 2.81 | w |
| 32.25 | 2.77 | w |
| 33.92 | 2.64 | m |
| 34.26 | 2.62 | m |
| 36.19 | 2.48 | w |
| 36.99 | 2.43 | w |
| 37.63 | 2.39 | w |
| 42.87 | 2.11 | w |
| 44.39 | 2.04 | w |
| 45.15 | 2.01 | w |
| 45.97 | 1.97 | w |
| 46.23 | 1.96 | w |
| 46.76 | 1.94 | w |
| 47.74 | 1.90 | w |

*impurity

Example 4

This sample is that of example 3 but has been additionally acid-washed according to the procedure above, which leads to some ion-exchange. The anhydrous composition is $H_xNa_{1.56}Nb_{1.14}Ti_{2.60}Si_2O_{12.83}$. Powder x-ray diffraction on this sample identified it as having the sitinakite structure. Representative diffraction lines for the material are shown in Table 3 below.

TABLE 3

| 2-Θ | d(Å) | $I/I_0$ % |
|---|---|---|
| 11.26 | 7.85 | vs |
| 14.76 | 6.00 | m |
| 15.94 | 5.56 | w |
| 17.62 | 5.03 | m |
| 18.56 | 4.78 | w |
| 21.81 | 4.07 | w |
| 25.29 | 3.52 | w |
| 26.44 | 3.37 | m |
| 27.14 | 3.28 | m |
| 27.48 | 3.24 | m |
| 29.76 | 3.00 | w |
| 31.94 | 2.80 | m |
| 32.19 | 2.78 | w |
| 33.10 | 2.70 | w |
| 33.94 | 2.64 | m |
| 34.22 | 2.62 | m |
| 36.14 | 2.48 | w |
| 36.88 | 2.44 | w |
| 37.44 | 2.40 | w |
| 45.32 | 2.00 | w |
| 45.94 | 1.97 | w |
| 46.18 | 1.96 | m |
| 46.82 | 1.94 | w |
| 47.64 | 1.91 | w |
| 48.38 | 1.88 | w |

Example 5

This sample has the sitinakite structure with the anhydrous composition $Na_{3.16}Ti_{2.77}Nb_{1.05}Si_2O_{13.74}$. Large batches of this material were prepared using the formulation: 0.95 $Na_2O$:0.15 $Nb_2O_5$:0.75 $TiO_2$:0.85 $SiO_2$:129 $H_2O$:3.0 i-PrOH: 3.4 EtOH A typical preparation used 50% NaOH solution, hydrous niobium pentoxide, Titanium isopropoxide, $Ti(OiPr)_4$, tetraethylorthosilicate (TEOS) and deionized water. The NaOH solution was diluted with water into which the hydrous niobium pentoxide was slurried. Then TEOS was slowly added with vigorous stirring and the reaction mixture homogenized for an additional 15 minutes post-addition. Then $Ti(OiPr)_4$ was slowly added and the reaction mixture homogenized further. The reaction mixture was transferred to a reactor and digested at 200° C. for 24 hr at autogenous pressure. The product was isolated by filtration, washed with deionized water and dried. Representative x-ray diffraction lines for the product are shown in table 4 below.

TABLE 4

| 2-Θ | d(Å) | $I/I_0$ % |
|---|---|---|
| 8.75 | 10.10 | w* |
| 9.99 | 8.85 | w* |
| 11.2 | 7.85 | vs |
| 14.69 | 6.03 | m |
| 15.93 | 5.56 | w |
| 17.58 | 5.04 | m |
| 18.58 | 4.77 | w |
| 22.68 | 3.92 | w |
| 25.30 | 3.52 | w |
| 25.98 | 3.43 | w |
| 26.42 | 3.37 | m |
| 27.10 | 3.29 | w |

TABLE 4-continued

| 2-Θ | d(Å) | I/I₀ % |
|---|---|---|
| 27.0 | 3.25 | m |
| 29.59 | 3.02 | w |
| 30.21 | 2.96 | w |
| 31.79 | 2.81 | w |
| 32.24 | 2.77 | w |
| 33.84 | 2.65 | m |
| 34.24 | 2.62 | m |
| 36.15 | 2.48 | w |
| 36.93 | 2.43 | w |
| 37.49 | 2.40 | w |
| 42.81 | 2.11 | w |
| 44.37 | 2.04 | w |
| 45.15 | 2.01 | w |
| 45.95 | 1.97 | w |
| 46.28 | 1.96 | w |
| 46.66 | 1.94 | w |
| 47.74 | 1.90 | w |

*impurity

Example 6

In a Teflon beaker, 12.46 g NaOH (99%) was dissolved in 139.39 g deionized water while stirring under the heidolph mixer. To this solution, 54.00 g Ludox AS-40 (40% $SiO_2$) was added in five pours over about a 5 minute period. The reaction mixture became thicker and more opaque with the additions. After 20 minutes of stirring, 21.06 g of $Ti(OiPr)_4$ (97%) was added fast dropwise using a 23 ml pipette. The reaction mixture became granular with the Ti addition and was allowed to stir 2 hours to homogenize. The initial reaction mixture was digested statically at autogenous pressure at 200° C. for 144 hours. White solid products were isolated by filtration washed with deionized water and dried. Characterization by powder X-ray diffraction identified the product as zorite. Representative X-ray diffraction lines are shown below in table 4. Elemental analysis showed the composition to be $Na_{1.86}TiSi_{2.69}O_{8.31}$. This as-synthesized material was tested for $Hg^{2+}$ uptake and is presented comparative example 5A. A portion of this product was acid washed before testing, according to the procedure given above and is the subject of Example 6.

TABLE 4

| 2-Θ | d(Å) | I/I₀ % |
|---|---|---|
| 7.64 | 11.56 | vs |
| 12.74 | 6.94 | vs |
| 12.92 | 6.85 | s |
| 16.86 | 5.25 | m |
| 19.94 | 4.45 | m |
| 24.80 | 3.59 | m |
| 25.98 | 3.43 | m |
| 26.36 | 3.38 | m |
| 26.74 | 3.33 | w |
| 27.96 | 3.19 | w |
| 29.04 | 3.07 | s |
| 29.24 | 3.05 | vs |
| 29.96 | 2.98 | s |
| 30.80 | 2.90 | m |
| 32.40 | 2.76 | m |
| 34.08 | 2.63 | m |
| 34.68 | 2.58 | m |
| 35.95 | 2.50 | w |
| 37.04 | 2.43 | m |
| 39.26 | 2.29 | w |
| 39.57 | 2.28 | w |
| 40.48 | 2.23 | w |
| 41.56 | 2.17 | w |
| 41.92 | 2.15 | w |

TABLE 4-continued

| 2-Θ | d(Å) | I/I₀ % |
|---|---|---|
| 42.46 | 2.13 | w |
| 43.08 | 2.10 | w |
| 44.76 | 2.02 | w |
| 45.58 | 1.99 | w |
| 47.00 | 1.93 | w |
| 48.06 | 1.89 | w |
| 48.50 | 1.88 | w |
| 50.84 | 1.79 | w |
| 51.45 | 1.77 | w |
| 52.57 | 1.74 | m |
| 53.88 | 1.70 | m |

A series of metallosilicate, modified metallosilicate and titanium oxide-based materials were also evaluated for their ability to remove $Hg^{2+}$ from solution. These are offered as comparative examples.

Comparative Example C1

In a Teflon beaker equipped with a high-speed stirrer, 101.64 g KOH (87.8%) was dissolved in 191.03 g deionized water. To this solution, added 79.64 g colloidal silica (Ludox AS-40, 40% $SiO_2$) in a single pour with vigorous stirring forming a translucent solution which turned clear after 2 hours of homogenization. To the clear solution, 77.69 g $Ti(OiPr)_4$ (97%) was added dropwise over 6 minutes. The reaction mixture turned to a white, opaque colloidal-like suspension with an additional 20 minutes of stirring. The reaction mixture was loaded into a 600 cc stirred autoclave and digested 120 hours at 175° C. stirring at 250 rpm. The solid products were isolated by centrifugation, washed with deionized water and dried at room temperature. The product was identified as titanium silicate pharmacosiderite via powder x-ray diffraction, accompanied by a slight $K_2TiSi_3O_9$ impurity. Representative x-ray diffraction lines for the product are shown in Table 5, with asterisks indicating peaks associated with the $K_2TiSi_3O_9$ impurity. Elemental analysis yielded the empirical formula $K_{1.75}TiSi_{1.06}O_{5.0}$. A portion of this product was ion-exchanged with NaCl prior to testing.

TABLE 5

| 2-Θ | d(Å) | I/I₀ % |
|---|---|---|
| 11.68 | 7.57 | vs |
| 15.70 | 5.64 | w* |
| 16.42 | 5.39 | w |
| 20.08 | 4.42 | w |
| 23.18 | 3.83 | m |
| 26.18 | 3.40 | w* |
| 28.40 | 3.14 | vs |
| 30.73 | 2.91 | w |
| 32.06 | 2.79 | w* |
| 32.92 | 2.72 | m |
| 34.83 | 2.57 | w |
| 36.84 | 2.44 | m |
| 38.81 | 2.32 | w |
| 40.38 | 2.23 | w* |
| 40.56 | 2.22 | w |
| 47.08 | 1.93 | w |
| 48.43 | 1.88 | m |
| 50.03 | 1.82 | w |

*$K_2TiSi_3O_9$ impurity

Comparative Example C2

In a Teflon beaker equipped with a high-speed stirrer, 73.34 g KOH (87.7%) was dissolved in 254.43 g deionized water. To this solution, 68.27 g colloidal silica (Ludox AS-40, 40% $SiO_2$) was added over 10 minutes with vigorous stirring, forming a white suspension. After 20 minutes of homogenization, 45.61 g zirconium acetate solution (22.1% $ZrO_2$) was added fast dropwise. After 10 minutes of homogenization, 5.35 g hydrous $Nb_2O_5$ (62.5%) was added and the reaction mixture was stirred for an additional 5 minutes. The reaction mixture was loaded into a 600 cc stirred autoclave and digested for 24 hours at 200° C. stirring at 250 RPM. The solid product was isolated by centrifugation, washed with deionized water and dried in air. X-ray powder diffraction revealed the product to have the umbite structure. Representative diffraction lines for the product are shown below in Table 6. Elemental analysis yielded the empirical formula $K_{2.15}Zr_{0.81}Nb_{0.19}Si_{3.34}O_{9.5}$. A portion of product was ion-exchanged with NaCl before use in testing.

TABLE 6

| 2-Θ | d(Å) | I/I₀ % |
|---|---|---|
| 10.82 | 8.17 | m |
| 13.32 | 6.64 | m |
| 14.90 | 5.94 | s |
| 16.34 | 5.42 | w |
| 17.00 | 5.21 | w-m |
| 18.08 | 4.90 | w |
| 20.02 | 4.43 | w-m |
| 21.78 | 4.08 | m |
| 24.54 | 3.63 | w |
| 25.03 | 3.56 | w |
| 26.40 | 3.37 | m |
| 28.38 | 3.14 | m |
| 28.96 | 3.08 | m |
| 29.50 | 3.03 | vs |
| 29.96 | 2.98 | s |
| 30.76 | 2.90 | m |
| 31.84 | 2.81 | w |
| 32.96 | 2.72 | w |

TABLE 6-continued

| 2-Θ | d(Å) | I/I₀ % |
|---|---|---|
| 34.14 | 2.62 | w |
| 34.94 | 2.57 | w-m |
| 37.62 | 2.39 | w |
| 38.10 | 2.36 | w |
| 41.52 | 2.17 | w |
| 42.56 | 2.12 | w |
| 43.22 | 2.09 | w |
| 45.58 | 1.99 | w |
| 46.06 | 1.97 | w |
| 48.74 | 1.87 | w |
| 49.74 | 1.83 | w |
| 50.22 | 1.82 | m |

Comparative Example C3

A series of sodium tin silicates were prepared as follows. To a Teflon beaker, 36.16 g colloidal silica (Ludox AS-40, 40% $SiO_2$) was added and placed under a high-speed stirrer. Then a solution was prepared by dissolving 19.26 g NaOH pellets in 90.00 g deionized water. This solution was added to the colloidal silica with vigorous stirring. The white reaction mixture was homogenized for 20 minutes post-addition. Separately, 21.10 g $SnCl_4 \cdot 5H_2O$ was dissolved in 83.48 g deionized water. This solution was added to the reaction mixture and mixed for an additional 20 minutes. The thin, white reaction mixture was split among four 125 mL Teflon-lined autoclaves and digested under static conditions at 200° C. for 3, 7, 14 and 21 days at autogenous pressures. The solid products were isolated via centrifugation, washed with deionized water and dried at room temperature. Powder X-ray diffraction was used to characterize the products, which were identified as Sn-gaidonnayite-like materials. Representative x-ray diffraction lines are shown for the products in Table 7.

TABLE 7

| Example C3A, 3 days | | | Example C3B, 7 days | | | Example C3C, 14 days | | | Example C3D, 21 days | | |
|---|---|---|---|---|---|---|---|---|---|---|---|
| 2-Θ | d(Å) | I/I₀ % | 2-Θ | d(Å) | I/I₀ % | 2-Θ | d(Å) | I/I₀ % | 2-Θ | d(Å) | I/I₀ % |
| 7.42 | 11.91 | s-vs | 7.46 | 11.84 | w | 7.52 | 11.74 | m | 7.58 | 11.65 | w-m |
| 11.12 | 7.95 | w-m | 14.10 | 6.28 | m | 14.04 | 6.30 | m | 14.06 | 6.29 | m |
| 18.88 | 4.70 | m | 15.25 | 5.81 | m | 15.22 | 5.82 | m-s | 15.26 | 5.80 | m |
| 32.21 | 2.78 | vs | 16.04 | 5.52 | m | 16.00 | 5.54 | m | 16.02 | 5.53 | m |
| 34.35 | 2.61 | m | 17.19 | 5.15 | w | 17.16 | 5.16 | w-m | 17.17 | 5.16 | m |
| 43.02 | 2.10 | m | 18.82 | 4.71 | w | 18.78 | 4.72 | w | 18.82 | 4.71 | w |
| | | | 20.84 | 4.26 | w | 20.78 | 4.27 | w-m | 20.80 | 4.27 | m |
| | | | 22.46 | 3.96 | w | 22.36 | 3.97 | w | 22.38 | 3.97 | w |
| | | | 27.02 | 3.30 | w | 23.66 | 3.76 | w | 27.00 | 3.30 | m |
| | | | 27.19 | 3.28 | w | 27.04 | 3.30 | m | 28.22 | 3.16 | w |
| | | | 29.38 | 3.04 | vs | 28.20 | 3.16 | w | 29.36 | 3.04 | vs |
| | | | 30.76 | 2.90 | m | 29.34 | 3.04 | vs | 30.76 | 2.90 | m |
| | | | 32.32 | 2.77 | m | 30.74 | 2.91 | m | 32.32 | 2.77 | m |
| | | | 32.67 | 2.74 | w | 32.28 | 2.77 | m | 34.00 | 2.63 | w |
| | | | 34.76 | 2.58 | w | 33.92 | 2.64 | m | 34.698 | 2.58 | w |
| | | | 36.77 | 2.44 | m | 34.68 | 2.58 | m | 36.74 | 2.44 | m |
| | | | 38.14 | 2.36 | w-m | 36.74 | 2.44 | w-m | 38.34 | 2.35 | w-m |
| | | | 38.34 | 2.35 | w-m | 38.07 | 2.36 | m | 41.66 | 2.17 | w |
| | | | 43.84 | 2.06 | w | 38.36 | 2.34 | w-m | 43.77 | 2.07 | m |
| | | | 48.66 | 1.87 | m | 41.35 | 2.18 | w | 45.64 | 1.99 | w |
| | | | | | | 41.66 | 2.17 | w | 46.88 | 1.94 | w |
| | | | | | | 43.76 | 2.07 | w | 48.06 | 1.89 | w |
| | | | | | | 48.60 | 1.87 | m | 48.66 | 1.87 | m |
| | | | | | | 49.24 | 1.85 | w | 49.34 | 1.85 | w |
| | | | | | | 49.72 | 1.83 | w | 49.78 | 1.83 | w |

Comparative Example C4

In a Teflon beaker, 19.54 g KOH (85.22%) was dissolved in 115.86 g deionized water using a Heidolph stirrer. Then 46.14 g colloidal silica (LUDOX AS-40, 40% $SiO_2$) was added in a single pour and allowed to stir for 10 minutes. This was followed by the addition of 30.0 g $Ti(OiPr)_4$ (97%). A brilliant white gel resulted which was allowed to homogenize further. The homogenous gel was distributed among three Teflon-lined Parr reactors and digested quiescently at a temperature of 200° C. for 46 hr at autogenous pressure. The solid products were isolated by centrifugation, washed with de-ionized water and dried at room temperature. The product was identified as Ti-umbite by powder x-ray diffraction. Representative diffraction lines are shown in Table 8 below. Elemental analysis yielded the empirical composition $K_{1.79}TiSi_{2.60}O_{8.1}$. The products were sodium ion-exchanged before they were tested.

TABLE 8

| 2-Θ | d(Å) | $I/I_0$ % |
|---|---|---|
| 11.26 | 7.85 | m |
| 13.72 | 6.45 | m |
| 14.20 | 6.23 | w |
| 15.33 | 5.77 | m |
| 17.92 | 4.95 | w |
| 19.21 | 4.62 | w |
| 20.60 | 4.31 | w |
| 21.83 | 4.07 | w |
| 22.49 | 3.95 | w |
| 22.90 | 3.88 | w |
| 24.96 | 3.57 | w |
| 25.76 | 3.46 | m |
| 26.51 | 3.36 | w |
| 27.44 | 3.25 | w |
| 27.89 | 3.20 | m |
| 28.54 | 3.13 | m |
| 29.80 | 3.00 | m |
| 30.34 | 2.94 | s |
| 30.62 | 2.92 | m |
| 30.88 | 2.89 | m |
| 31.66 | 2.82 | s |
| 32.56 | 2.75 | w |
| 32.94 | 2.72 | m |
| 33.82 | 2.65 | w |
| 35.42 | 2.53 | w |
| 35.84 | 2.50 | w |
| 36.50 | 2.46 | w |
| 37.74 | 2.38 | w |
| 38.44 | 2.34 | w |
| 38.64 | 2.33 | w |
| 38.92 | 2.31 | w |
| 39.10 | 2.30 | m |
| 39.58 | 2.28 | w |
| 41.32 | 2.18 | w |
| 42.12 | 2.14 | w |
| 42.72 | 2.11 | w |
| 44.50 | 2.03 | w |
| 45.05 | 2.01 | w |
| 45.86 | 1.98 | w |
| 46.32 | 1.96 | w |
| 47.07 | 1.93 | w |
| 47.71 | 1.90 | w |
| 50.27 | 1.81 | w |
| 51.06 | 1.79 | w |
| 51.84 | 1.76 | w |
| 52.38 | 1.75 | w |
| 52.68 | 1.74 | w |
| 53.30 | 1.72 | w |
| 54.62 | 1.68 | w |
| 55.40 | 1.66 | w |
| 55.58 | 1.65 | w |

Comparative Example C5B

See Example 6 for Comparative Example 5A

The alkoxides TEOS (98%), 38.00 g, and $Ti(OiPr)_4$ (97%), 10.48 g were mixed in a Teflon beaker placed under a high-speed stirrer. Separately, 5.89 g NaOH (99%) was dissolved in 85.00 g deionized water. This solution was added rather quickly to the stirring reaction mixture, dropperwise, using a 23 ml dropper. After the addition of a few dropper volumes of NaOH solution, the addition was stopped and the reaction mixture allowed to stir a few minutes as a gel had formed. Then addition was continued to completion. The thick gel was then stirred for 2 hr to facilitate homogenization of the gel. The reaction mixture was transferred to two Parr Teflon-lined reactors and digested at 200° C. for 140 hr, quiescently at autogenous pressure. The products were isolated by centrifugation, washed with deionized water and dried at room temperature. Characterization of the solid by powder x-ray diffraction showed the material to have the zorite topology. Representative x-ray diffraction lines for the product are given in Table 9 below. The composition was $Na_{1.96}TiSi_{2.71}O_{8.4}$.

TABLE 9

| 2-Θ | d(Å) | $I/I_0$ % |
|---|---|---|
| 7.62 | 11.59 | m |
| 12.72 | 6.95 | s-vs |
| 12.92 | 6.85 | m-s |
| 16.87 | 5.25 | m |
| 19.91 | 4.46 | w-m |
| 24.84 | 3.58 | m |
| 26.02 | 3.42 | m |
| 26.36 | 3.38 | m |
| 29.06 | 3.07 | m-s |
| 29.28 | 3.05 | vs |
| 29.94 | 2.98 | s |
| 30.79 | 2.90 | m |
| 32.38 | 2.76 | m |
| 34.08 | 2.63 | m |
| 34.66 | 2.59 | m |
| 35.94 | 2.50 | w |
| 36.79 | 2.44 | w |
| 37.03 | 2.43 | w |
| 39.26 | 2.29 | w |
| 39.58 | 2.28 | w |
| 41.62 | 2.17 | w |
| 41.88 | 2.16 | w |
| 42.52 | 2.12 | w |
| 43.10 | 2.10 | w |
| 44.74 | 2.02 | w |
| 46.97 | 1.93 | w |
| 48.04 | 1.89 | w |
| 48.50 | 1.88 | w |
| 50.89 | 1.79 | w |
| 51.52 | 1.77 | w |
| 52.26 | 1.75 | w |
| 52.60 | 1.74 | m |
| 53.90 | 1.70 | m |

Comparative Example C6

A solution was prepared by dissolving 11.31 g NaOH pellets in 20 g deionized water. To this solution, 3.59 g $LiOH*H_2O$ (Aldrich) was added with vigorous stirring. After 20 minutes of homogenization, added 27.84 g colloidal silica (Ludox AS-40, 40% $SiO_2$) dropwise over 10 minutes. Separately, a solution was prepared by dissolving 16.25 g $SnCl_4*5H_2O$ in 20.7 g $H_2O$. After 1 hour of homogenization, this solution was added to the white suspension and mixed for an additional 20 minutes post addition. The creamy reaction mixture was loaded into a 125 mL autoclave and digested 16 days at 200° C. quiescently at autogenous pressure. The solid product was isolated by centrifugation, washed with deionized water and dried at room temperature. The product was analyzed via powder x-ray diffraction and representative x-ray diffraction lines for the product are listed in Table 10 below. A portion of the product was sodium ion exchanged before testing.

TABLE 10

| 2-Θ | d(Å) | I/I$_0$ % |
|---|---|---|
| 14.50 | 6.10 | m |
| 16.22 | 5.46 | m |
| 19.14 | 4.63 | w-m |
| 20.44 | 4.34 | w |
| 24.99 | 3.56 | w |
| 27.06 | 3.29 | m |
| 29.82 | 2.99 | vs |
| 33.22 | 2.69 | m |
| 35.62 | 2.52 | w |
| 37.10 | 2.42 | m |
| 38.82 | 2.32 | w |
| 41.90 | 2.15 | w |
| 44.54 | 2.03 | m |
| 46.98 | 1.93 | w |
| 47.56 | 1.91 | m |
| 49.46 | 1.84 | w |
| 49.83 | 1.83 | w |
| 51.56 | 1.77 | w |
| 53.86 | 1.70 | w |
| 54.36 | 1.69 | w |

Comparative Example C7

A potassium titanate composite consisting of mostly potassium octatitanate, $K_2Ti_8O_{17}$, some potassium hexatitanate, $K_2Ti_6O_{13}$, and some anatase, $TiO_2$, was used in this study. The sample was characterized by powder x-ray diffraction. Representative x-ray diffraction lines are shown in table 11.

TABLE 11

| 2-Θ | d(Å) | I/I$_0$ % |
|---|---|---|
| 11.14 | 7.94 | s |
| 11.46 | 7.72 | m-s |
| 12.04 | 7.34 | w |
| 13.82 | 6.40 | w |
| 19.77 | 4.49 | w |
| 24.10 | 3.69 | w |
| 25.30 | 3.52 | vs |
| 28.91 | 3.09 | m |
| 29.25 | 3.05 | m |
| 29.93 | 2.98 | w |
| 31.99 | 2.80 | w |
| 33.13 | 2.70 | w |
| 34.70 | 2.58 | w |
| 36.93 | 2.43 | w |
| 37.79 | 2.38 | m |
| 38.57 | 2.33 | w |
| 43.02 | 2.10 | w |
| 43.51 | 2.08 | w |
| 47.68 | 1.91 | m |
| 48.04 | 1.89 | m |
| 49.17 | 1.85 | w |
| 53.87 | 1.70 | w-m |
| 55.06 | 1.67 | w-m |

Comparative Examples C8A, C8B

A Teflon beaker was charged with 150.00 g TEAOH (35%) and began stirring with a high-speed stirrer. Next, 53.05 g TEOS (98%) was added dropperwise and allowed to stir for 2 hr to hydrolyze TEOS. Separately, 11.72 g $ZrOCl_{22}*8H_2O$ was dissolved in 25.00 g deionized water. This solution was added to the reaction mixture in a dropwise fashion, intermittently. Over the course of the addition a white gel formed. This was homogenized further for 2 hours. A solution was prepared dissolving 14.40 g CsOAc (95%) in 25.00 g deionized water. This solution was added quickly to the reaction mixture. The reaction mixture was transferred to Teflon-lined Parr reactors and digested at 175° C. for 48 (Example C8A) and 96 hr (Example C8B). The products were isolated by centrifugation, washed with deionized water and dried in air. Powder X-ray diffraction showed the products to be amorphous. The products were ion exchanged with sodium before testing.

Comparative Example C9

In a Teflon beaker under a high-speed stirrer, 22.76 g NaOH pellets was dissolved in 357.45 g deionized water. To this solution, 41.38 g colloidal silica (Ludox AS-40, 40% $SiO_2$) was added over a period of 10 minutes with vigorous stirring, forming a white suspension. After 20 minutes of homogenization, 28.44 g zirconium acetate solution (22.1 wt % $ZrO_2$) was added and contents stirred for an additional 3 minutes. The reaction mixture was loaded into a 600 cc stirred autoclave and digested for 72 hours at 200° C. while stirring at 250 RPM. The solid products were isolated by centrifugation, washed with deionized water and dried at room temperature. The product was identified as Zr-gaidonnayite via x-ray diffraction. Representative diffraction lines for the product are shown in table 12 below. Elemental analysis yielded the empirical composition $Na_{2.19}ZrSi_{3.28}O_{9.66}$.

TABLE 12

| 2-Θ | d(Å) | I/I$_0$ % |
|---|---|---|
| 13.88 | 6.37 | m |
| 15.12 | 5.86 | vs |
| 15.80 | 5.60 | m-s |
| 20.58 | 4.31 | w |
| 26.72 | 3.33 | w |
| 27.65 | 3.22 | w |
| 28.68 | 3.11 | vs |
| 30.54 | 2.93 | m-s |
| 31.18 | 2.87 | w-m |
| 31.81 | 2.81 | w-m |
| 34.10 | 2.63 | w |
| 36.12 | 2.48 | w |
| 37.46 | 2.40 | w |
| 41.14 | 2.19 | w |
| 43.12 | 2.10 | w |
| 44.59 | 2.03 | w |
| 48.00 | 1.89 | w-m |

Comparative Example C10

In a make-up tank, the preparation starts by dissolving 484 g NaOH (99%) pellets in 10909 g deionized water. Next 4150 g sodium silicate solution, (9.09% $Na_2O$, 29.3% $SiO_2$) is added to the sodium hydroxide solution and stirred until mixed. With vigorous stirring, using a dropping funnel, 2458 g zirconium acetate solution (20.26% $ZrO_2$ in 10% acetic acid) is added to the reaction mixture over a period of 15 minutes. The slurry is stirred and then transferred to the 5-gallon stirred reactor. The reactor is sealed and with stirring, the reaction mixture is ramped to 200° C. over a period of 6 hr. The reaction mixture is digested at 200° C. for 72 hr before it is cooled to room temperature. The product is isolated by filtration, thoroughly washed with 0.001 M NaOH solution and dried at 100° C. Powder X-ray diffraction showed the product to have the UZSi-9 structure. Representative lines in the x-ray diffraction pattern are shown below in Table 13. The isolated UZSi-9 had the composition $Na_{2.15}ZrSi_{3.45}O_{9.98}$.

C. while stirring at 250 RPM. The white product was isolated and washed via centrifugation. The solids were dried at room temperature and analyzed by powder X-ray diffraction. The solids were shown to be Sn silicate umbite by x-ray diffraction. Representative x-ray diffraction lines are given in Table 14. A portion of product was sodium ion exchanged, yielding the composition $K_{0.30}Na_{1.79}SnSi_{2.99}O_{9.03}$ for testing.

TABLE 13

| 2-Θ | d(Å) | I/I₀ |
|---|---|---|
| 12.04 | 7.34 | w |
| 13.92 | 6.36 | m |
| 15.58 | 5.68 | s |
| 17.08 | 5.19 | w |
| 19.74 | 4.49 | w |
| 22.12 | 4.02 | w |
| 23.20 | 3.83 | w |
| 24.26 | 3.67 | w |
| 25.26 | 3.52 | w |
| 26.24 | 3.39 | m |
| 28.96 | 3.08 | vs |
| 30.68 | 2.91 | w |
| 31.46 | 2.84 | w |
| 32.26 | 2.77 | m |
| 33.02 | 2.71 | w |
| 34.56 | 2.59 | w |
| 35.35 | 2.54 | w |
| 36.04 | 2.49 | m |
| 36.70 | 2.45 | w |
| 38.10 | 2.36 | w |
| 38.80 | 2.32 | w |
| 40.78 | 2.21 | w |
| 41.37 | 2.18 | w |
| 42.00 | 2.15 | w |
| 42.64 | 2.12 | w |
| 43.28 | 2.09 | m |
| 43.90 | 2.06 | w |
| 45.12 | 2.01 | w |
| 45.68 | 1.98 | m |
| 46.26 | 1.96 | m |
| 46.86 | 1.94 | w |
| 47.96 | 1.90 | w |
| 48.56 | 1.87 | w |
| 50.24 | 1.81 | w |
| 50.77 | 1.80 | w |
| 51.32 | 1.78 | w |
| 52.38 | 1.75 | w |
| 52.92 | 1.73 | w |
| 53.98 | 1.67 | w |
| 55.50 | 1.65 | w |

TABLE 14

| 2-Θ | d(Å) | I/I₀ |
|---|---|---|
| 11.20 | 7.89 | w |
| 13.64 | 6.49 | m |
| 15.34 | 5.77 | m |
| 16.80 | 5.27 | w |
| 17.72 | 5.00 | w |
| 18.48 | 4.80 | w |
| 20.50 | 4.33 | m |
| 22.36 | 3.97 | w |
| 22.76 | 3.90 | w |
| 25.06 | 3.55 | w |
| 25.58 | 3.48 | w |
| 25.98 | 3.43 | w |
| 27.52 | 3.24 | m |
| 28.80 | 3.10 | w |
| 29.44 | 3.03 | m |
| 30.12 | 2.96 | vs |
| 30.78 | 2.90 | m |
| 31.52 | 2.84 | m |
| 32.58 | 2.75 | w |
| 33.74 | 2.65 | w |
| 35.08 | 2.56 | m |
| 35.42 | 2.53 | w |
| 36.08 | 2.49 | w |
| 36.36 | 2.47 | w |
| 37.44 | 2.40 | w |
| 37.92 | 2.37 | w |
| 38.46 | 2.34 | w |
| 38.96 | 2.31 | w |
| 39.48 | 2.28 | w |
| 40.86 | 2.21 | w |
| 41.44 | 2.18 | w |
| 42.04 | 2.15 | w |
| 42.42 | 2.13 | w |
| 43.46 | 2.08 | w |
| 44.12 | 2.05 | w |
| 44.60 | 2.03 | w |
| 45.73 | 1.98 | w |
| 47.36 | 1.92 | m |
| 48.96 | 1.86 | w |
| 49.80 | 1.83 | w |

Comparative Example C11

The sample of comparative example C10 was modified by the acid treatment procedure given at the beginning of the examples.

Comparative Example C12

A solution was prepared by dissolving 86.85 g KOH (87.8%) in 144.84 g deionized water. This solution was added fast dropwise to a Teflon beaker charged with 81.66 g Ludox AS-40 while stirring vigorously with a high-speed mechanical stirrer, forming a dual phase suspension. After 20 minutes of homogenization, the reaction mixture was clear. A solution prepared by dissolving 36.65 g $SnCl_4*5H_2O$ in 100 g deionized water was then added to the reaction mixture in a dropwise fashion over 5 minutes with vigorous stirring. The clear solution was stirred for an additional 10 minutes. The clear solution was loaded into a 600 cc stirred Parr reactor and digested for 36 hours at 200°

Example 7 $Hg^{2+}$ Removal from Solution

The samples disclosed in the examples above were tested to determine their ability to adsorb $Hg^{2+}$ by determining the distributions ($K_d$) for each of the metals between adsorption on the solid vs. remaining in the solution state. The $Hg^{2+}$ test solution was prepared by dissolving mercuric acetate in tap water. Several different mercury-containing test solutions were used for the $Hg^{2+}$ uptake evaluation. In the simplest test, Test 1, the test solution was prepared by dissolving 44.4 mg mercuric acetate in 999.54 g tap water. Analysis showed the test solution employed in Test 1 contained 27 ppm $Hg^{2+}$, 31 ppm $Ca^{2+}$ and 10 ppm $Mg^{2+}$. Also prepared with tap water containing $Mg^{2+}$ and $Ca^{2+}$, the Test 2 solution contained added metals $Hg^{2+}$, $Pb^{2+}$, $Co^{2+}$, $Cr^{3+}$, $Cd^{2+}$, and $Sr^{2+}$. The concentrations of metals in Test 2 were $Mg^{2+}$(27.3 ppm), $Ca^{2+}$(32.8 ppm), $Hg^{2+}$(30.0 ppm), $Cr^{3+}$(13.6 ppm), $Cd^{2+}$(22.4 ppm), $Pb^{2+}$(13.5 ppm), $Sr^{2+}$(24.1 ppm) and $Co^{2+}$ (23.5 ppm). For the tests, 200 mg of ion-exchanger is placed in a 30 ml borosilicate vial to which 20 ml of $Hg^{2+}$- containing test solution is added using a 20 ml syringe. The loaded vial is sealed with a cap and placed in a Bohdan shaker and shaken vigorously for 24 hours at room temperature. Once the ion-exchanger has been contacted with the $Hg^{2+}$ solution for the desired amount of time, the solution/solid suspension is removed from the vial using a syringe. Solids were separated from the solution by pushing the syringe contents through a 0.45 um Nylon filter. The solution was collected in a plastic vial and sent for chemical analysis via ICP or ICP/mass spec. The detection level for $Hg^{2+}$ was 20 ppb. It was assumed that the disappearance of the metals from solution were due to adsorption by the solid.

The $K_d$ value for the distribution was calculated using the following formula:

$$K_d \text{ (mL/g)} = \frac{(V)(Ac)}{(W)(Sc)}1$$

where: V=volume of waste simulant (mL)
Ac=concentration of cation absorbed on ion-exchanger (g/mL)
W=mass of ion-exchanger evaluated (g)
Sc=concentration of cation in post reaction supernate (g/mL)

Table 15 below summarizes the results of the uptake studies.

TABLE 15

$Hg^{2+}$ distribution expressed as $K_d$ values

| Sample Example | Test 1 $Hg^{2+}$ $K_d$ (mg/ml) | Test 2 $Hg^{2+}$ $K_d$ (mg/ml) |
|---|---|---|
| 1 | — | 15943 |
| 2 | — | 11221 |
| 3 | 5300 | 3400 |
| 4 | — | 7468 |
| 5 | 2900 | 2446 |
| 6 | 51787 | — |
| C1 | 1488 | 1264 |
| C2 | 255 | 362 |
| C3A | 131 | 131 |
| C3B | 181 | 173 |
| C3C | 135 | 260 |
| C3D | 200 | 317 |
| C4 | 1488 | 977 |
| C5A | 419 | 241 |
| C5B | 400 | 261 |
| C6 | 47 | 30 |
| C7 | — | 150 |
| C8A | 56 | 88 |
| C8B | 48 | 50 |
| C9 | 17 | — |
| C10 | 25 | — |
| C11 | 10 | — |
| C12 | 16 | — |

Comparative Example 13

Although it has been pointed out that aluminosilicate zeolites are not suitable for the present application because of their instability in blood or gastrointestinal fluids, we illustrate here the differences in selectivity for $Hg^{2+}$ and $Pb^{2+}$ removal zeolite X exhibits. We have established in U.S. Pat. No. 9,233,856 that high charge density zeolites, Si/Al=1 species like zeolite 4A or zeolite X are not selective for mercury, but lower charge density zeolites with Si/Al=3-10 are preferred. Meanwhile, zeolite X is extremely effective for removing $Pb^{2+}$ from solution (Zeolite 4A was not tested with $Pb^{2+}$). We include in table 16 below the data for Zeolite X, which was also tested in Test 2 described in Example 7 above. The detection level for $Pb^{2+}$ in Test 2 is 0.2 ppm. This demonstrates that the heavy metals cannot be grouped together as a single class concerning their removal by ion-exchangers; the ion exchangers that remove $Hg^{2+}$ are often very different from those that will remove $Pb^{2+}$ and other heavy metals. Note that the $K_d$=100 for $Hg^{2+}$ uptake by Zeolite X shows equal preference for being adsorbed on the solid vs. staying in solution, since (Ac)/(Sc)=1.

TABLE 16

$Hg^{2+}$ and $Pb^{2+}$ distribution expressed as $K_d$ values for Zeolite X in Test 2

| Sample | $Hg^{2+}$ $K_d$ | $Pb^{2+}$ $K_d$ |
|---|---|---|
| Zeolite X, Si/Al = 1 | 100 | >6650 |

Comments on the Examples

Our standard for acceptable $Hg^{2+}$ removal is that the ion exchanger removes at least 95% of the mercury from solution in these tests, which corresponds to $K_d$=1900. The examples and the comparative examples illustrate several points concerning $Hg^{2+}$ removal by the class of ion exchanger materials, the titanium, zirconium and tin oxides and silicates that are stable in blood and gastrointestinal fluids and therefore possibly suitable for removing $Hg^{2+}$ from these fluids.

As a class that is sampled widely, the comparative examples show that these materials are very poor for removing $Hg^{2+}$ from the test solutions. The class of titanium, zirconium and tin silicates contain octahedral Ti, Zr and Sn, often in the form of $[MO_{6/2}]^{2-}$ in high concentration, leading to highly negatively charged frameworks that are generally not effective. Our work with $Hg^{2+}$ remediation using zeolites (U.S. Pat. No. 9,233,856) and manganese oxides (U.S. Pat. No. 9,150,436) supports this as high charge density frameworks were not effective for removing $Hg^{2+}$. While the titanium, zirconium, tin silicates and oxides have the proper stability to remove $Hg^{2+}$, from bodily fluids, very few show high affinity for $Hg^{2+}$ and significant ability to remove it from solution. An exception to this seems to be titanium silicates with the sitinakite topology, which is also a high charge density framework. These showed significant affinity for $Hg^{2+}$ both in the as-synthesized form, the Nb-substituted form and in the acid treated or partially proton exchanged forms. Compositions with this particular topology, the sitinakite structure, shows genuine affinity for $Hg^{2+}$ under conditions that are similar to those encountered in human blood and is markedly different from the other materials in the class of titanium, zirconium and tin oxides and silicates. Utility in $Hg^{2+}$ removal also cannot be generalized among the oxides. In Example 1, sodium nonatitanate is shown to have excellent affinity for removing $Hg^{2+}$ from the test solutions. Yet potassium octatitanate, presented in example C7, showed no affinity for $Hg^{2+}$ in the tests. We limit our claims to the sodium nonatitanate for this application of $Hg^{2+}$ removal from bodily fluids. A high charge density titanium silicate with the zorite topology is presented in Comparative Examples 5A (see example 6) and 5B. Neither of these as-synthesized materials shows particularly good affinity for $Hg^{2+}$ uptake in the tests. In Example 6, the acid treated version of the material of Comparative Example 5A shows excellent affinity for $Hg^{2+}$. In examples 3 and 4, we also see an improvement in $Hg^{2+}$ uptake in a sitinakite topology material after treatment with acid. This phenomenon is not general, Comparative Examples 10 and 11 show that UZSi-9 is not effective in $Hg^{2+}$ remediation before or after acid treatment.

Specific Embodiments

While the following is described in conjunction with specific embodiments, it will be understood that this description is intended to illustrate and not limit the scope of the preceding description and the appended claims.

A first embodiment of the invention is a process for removing $Hg^{2+}$ from bodily fluids comprising contacting the fluid containing the toxins with an ion exchanger to remove the toxins from the fluid by ion exchange between the ion exchanger and the bodily fluid, the titanium metallate ion exchanger selected from the group consisting of the sodium nonatitanate, sitinakite, acid-treated zorite topologies and mixtures thereof, the composite metallate having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11. An embodiment of the invention is one, any or all of prior embodiments in this paragraph up through the first embodiment in this paragraph wherein the bodily fluid is selected from the group consisting of whole blood, blood plasma, or other component of blood, gastrointestinal fluids and dialysate solution containing blood, blood plasma, other component of blood or gastrointestinal fluids. An embodiment of the invention is one, any or all of prior embodiments in this paragraph up through the first embodiment in this paragraph where a>0. An embodiment of the invention is one, any or all of prior embodiments in this paragraph up through the first embodiment in this paragraph where x=0. An embodiment of the invention is one, any or all of prior embodiments in this paragraph up through the first embodiment in this paragraph where a+x=0. An embodiment of the invention is one, any or all of prior embodiments in this paragraph up through the first embodiment in this paragraph where A is a mixture of calcium and sodium. An embodiment of the invention is one, any or all of prior embodiments in this paragraph up through the first embodiment in this paragraph wherein the ion exchanger is packed into hollow fibers incorporated into a membrane. An embodiment of the invention is one, any or all of prior embodiments in this paragraph up through the first embodiment in this paragraph wherein the ion exchanger is contained on particles coated with a coating comprising a cellulose derivative composition. An embodiment of the invention is one, any or all of prior embodiments in this paragraph up through the first embodiment in this paragraph wherein the process is a hemoperfusion process wherein the bodily fluid is passed through a column containing the ion exchanger. An embodiment of the invention is one, any or all of prior embodiments in this paragraph up through the first embodiment in this paragraph wherein a dialysate solution is introduced into a peritoneal cavity and then is flowed through at least one adsorbent bed containing at least one of the ion exchanger. An embodiment of the invention is one, any or all of prior embodiments in this paragraph up through the first embodiment in this paragraph wherein the ion exchanger is formed into a shaped article to be ingested orally, followed by ion exchange between the ion exchanger and the $Hg^{2+}$ toxins contained in a gastrointestinal fluid in a mammal's intestines and then by excretion of the ion exchanger containing the toxins. An embodiment of the invention is one, any or all of prior embodiments in this paragraph up through the first embodiment in this paragraph wherein the shaped article is coated with a coating that is not dissolved by conditions within a stomach.

A second embodiment of the invention is a composition comprising a combination of a bodily fluid, a dialysate solution or a mixture of the bodily fluid and the dialysate solution the combination further comprising a titanium metallate ion exchanger selected from the group consisting of the sodium nonatitanate, sitinakite, acid-treated zorite topologies and mixtures thereof, the composite metallate having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11. An embodiment of the invention is one, any or all of prior embodiments in this paragraph up through the second embodiment in this paragraph wherein the bodily fluid is whole blood, blood plasma, other blood component or gastrointestinal fluid.

A third embodiment of the invention is an apparatus comprising a matrix containing a support material for a titanium metallate ion exchanger selected from the group consisting of the sodium nonatitanate, sitinakite, acid-treated zorite topologies and mixtures thereof, the composite metallate having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.6, "x" is the mole ratio of Si to Ti and has a value from 0 to 3, and "y" has a value from 2.05 to 11. An embodiment of the invention is one, any or all of prior embodiments in this paragraph up through the third embodiment in this paragraph wherein the matrix comprises a porous network comprising biocompatible polymers and metal oxides and silicates. An embodiment of the invention is one, any or all of prior embodiments in this paragraph up through the third embodiment in this paragraph wherein the biocompatible polymers comprise cross-linked carbohydrates or proteins. An embodiment of the invention is one, any or all of prior embodiments in this paragraph up through the third embodiment in this paragraph wherein the biocompatible polymer is a polysaccharide selected from α-glucans having 1,3-, 1,4- or 1,6-linkages. An embodiment of the invention is one, any or all of prior embodiments in this paragraph up through the third embodiment in this paragraph wherein the biocompatible polymer is a carbohydrate selected from glucose, fructose, sucrose, maltose, arabinose, mannose, galactose, lactose and oligomers and polymers comprising one or more of the carbohydrates. An embodiment of the invention is one, any or all of prior embodiments in this paragraph up through the third embodiment in this paragraph wherein the biocompatible polymer comprises a protein selected from albumin, ovalbumin, casein, myosin, actin, globulin, hemoglobin, myoglobin, gelatin and small peptides.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

We claim as our invention:

1. A process for removing $Hg^{2+}$ toxins from bodily fluids selected from the group consisting of blood, gastrointestinal fluids and dialysate solution comprising contacting the fluid containing the toxins with an ion exchanger at ion exchange conditions thereby removing at least 95% of the $Hg^{2+}$ from the fluid, the ion exchanger selected from the group consisting of a titanium metallates, the metallates respectively having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.60, "x" is the mole ratio of Si to Ti has a value from 0 to 3, and "y" has a value from 2.05 to 11 and wherein said titanium metallate has a topology selected from the group consisting of sodium nonatitanate, sitinakite, acid treated zorite and mixtures thereof.

2. The process of claim 1 wherein the bodily fluid is selected from the group consisting of whole blood, blood plasma, or other component of blood, gastrointestinal fluids and dialysate solution containing blood, blood plasma, other component of blood or gastrointestinal fluids.

3. The process of claim 1 where a=0 and the ion exchanger is titanium silicate with the sitinakite topology or acid treated titanium silicate with the sitinakite topology.

4. The process of claim 1 where a>0 and the ion exchanger is titanium niobium silicate with the sitinakite topology or acid treated titanium niobium silicate with the sitinakite topology.

5. The process of claim 1 where a=0 and the ion exchanger is acid treated titanium silicate with the zorite topology.

6. The process of claim 1 where a>0 and the ion exchanger is acid treated titanium niobium silicate with the zorite topology.

7. The process of claim 1 where x=0, a=0 and the ion exchanger is a titanium oxide with the sodium nonatitanate topology.

8. The process of claim 1 where x=0, a>0, and the ion exchanger is a titanium niobium oxide with the sodium nonatitanate topology.

9. The process of claim 1 where A is sodium, calcium, magnesium, hydronium ion or mixtures thereof.

10. The process of claim 1 wherein the ion exchanger is packed into hollow fibers incorporated into a membrane.

11. The process of claim 1 wherein said process is a hemoperfusion process wherein said bodily fluid is sent through a column containing said ion exchanger.

12. The process of claim 1 wherein said ion exchanger regenerates a dialysate solution.

13. The process of claim 1 wherein a dialysate solution is introduced into a peritoneal cavity and then is flowed through at least one adsorbent bed containing at least one of said ion exchanger.

14. The process of claim 1 wherein said ion exchanger is formed into a shaped article to be ingested orally and to pick up said toxins from a gastrointestinal fluid in a mammal's intestines followed by excretion of said shaped article containing said toxins.

15. The process of claim 14 wherein said shaped article is coated with a coating that is not dissolved by conditions within a stomach.

16. The process of claim 1 wherein said process is continuous ambulatory peritoneal dialysis or automated peritoneal dialysis.

17. A composition for removing at least 95% of $Hg^{2+}$ toxins from bodily fluids selected from the group consisting of blood, gastrointestinal fluids and dialysate solution, the composition comprising an ion exchanger selected from the group consisting of a titanium metallates, the metallates respectively having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.60, "x" is the mole ratio of Si to Ti has a value from 0 to 3, and "y" has a value from 2.05 to 11 and wherein said titanium metallate has a topology selected from the group consisting of sodium nonatitanate, sitinakite, acid treated zorite and mixtures thereof.

18. An apparatus for removing at least 95% of $Hg^{2+}$ toxins from bodily fluids from the group consisting of blood, gastrointestinal fluids and dialysate solution, the apparatus comprising an ion exchanger selected from the group consisting of a titanium metallates, the metallates respectively having an empirical formula on an anhydrous basis of:

$$A_m TiNb_a Si_x O_y$$

where A is an exchangeable cation selected from the group consisting of potassium ion, sodium ion, rubidium ion, cesium ion, calcium ion, magnesium ion, hydronium ion or mixtures thereof, "m" is the mole ratio of A to Ti and has a value from 0.10 to 3, "a" is the mole ratio of Nb to Ti and has a value from zero to 0.60, "x" is the mole ratio of Si to Ti has a value from 0 to 3, and "y" has a value from 2.05 to 11 and wherein said titanium metallate has a topology selected from the group consisting of sodium nonatitanate, sitinakite, acid treated zorite and mixtures thereof; and a matrix containing a support material for said ion exchanger.

19. The apparatus of claim 18 wherein said matrix comprises a porous network comprising biocompatible polymers and metal oxides and silicates.

20. The apparatus of claim 19 wherein said biocompatible polymers comprise cross-linked carbohydrates or proteins.

* * * * *